United States Patent
Tan et al.

(10) Patent No.: US 11,911,592 B2
(45) Date of Patent: Feb. 27, 2024

(54) SAFETY DRIP CHAMBER SPIKE WITH BREAKABLE FEATURE

(71) Applicant: CareFusion 303, Inc., San Diego, CA (US)

(72) Inventors: Benjamin Yang Teck Tan, Singapore (SG); Mum Pew Ng, Singapore (SG)

(73) Assignee: CareFusion 303, Inc., San Diego, CA (US)

( * ) Notice: Subject to any disclaimer, the term of this patent is extended or adjusted under 35 U.S.C. 154(b) by 392 days.

(21) Appl. No.: 17/115,354

(22) Filed: Dec. 8, 2020

(65) Prior Publication Data
US 2022/0176035 A1 Jun. 9, 2022

(51) Int. Cl.
*A61M 5/162* (2006.01)
*A61M 5/14* (2006.01)

(52) U.S. Cl.
CPC .......... *A61M 5/162* (2013.01); *A61M 5/1411* (2013.01); *A61M 2205/02* (2013.01); *A61M 2207/10* (2013.01)

(58) Field of Classification Search
CPC ... A61M 5/162; A61M 5/1626; A61M 5/1411
See application file for complete search history.

(56) References Cited

U.S. PATENT DOCUMENTS

| | | | |
|---|---|---|---|
| 4,675,020 A * | 6/1987 | McPhee | A61J 1/2089 604/414 |
| 5,024,659 A * | 6/1991 | Sjostrom | A61M 25/065 604/110 |
| 5,279,605 A | 1/1994 | Karrasch et al. | |
| 5,971,972 A * | 10/1999 | Rosenbaum | A61J 1/10 604/411 |
| 6,709,424 B1 | 3/2004 | Knierbein | |
| 7,470,265 B2 * | 12/2008 | Brugger | A61M 5/162 604/413 |
| 2003/0083640 A1 * | 5/2003 | Sadiow | A61M 5/1411 604/409 |
| 2009/0204080 A1 | 8/2009 | Balteau et al. | |
| 2013/0237949 A1 * | 9/2013 | Miller | A61M 5/3278 604/110 |

FOREIGN PATENT DOCUMENTS

| | | | | |
|---|---|---|---|---|
| EP | 0174011 B1 * | 6/1990 | | A61M 5/162 |
| WO | WO-2019018284 A1 * | 1/2019 | | A61J 1/10 |

OTHER PUBLICATIONS

International Search Report and Written Opinion for Application No. PCT/US2021/062045, dated Mar. 29, 2022, 13 pages.

* cited by examiner

*Primary Examiner* — Catharine L Anderson
*Assistant Examiner* — Arjuna P Chatrathi
(74) *Attorney, Agent, or Firm* — Morgan, Lewis & Bockius LLP

(57) ABSTRACT

An intravenous (IV) spike for administering a medicinal fluid from a container may include a head portion at a proximal end thereof, a base portion at a distal end thereof, and an elongate body portion connecting the head and the base portions. The elongate body portion may be configured to be coupled to the container. The IV spike may further include a radial notch extending at least partially along a circumference of an outer surface of the elongate body portion. The radial notch may be recessed radially inward from the outer surface.

8 Claims, 3 Drawing Sheets

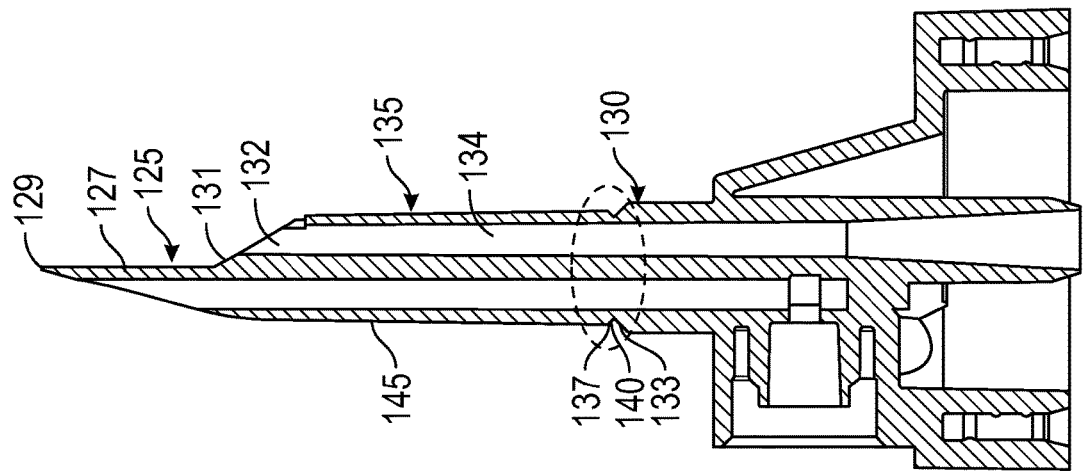
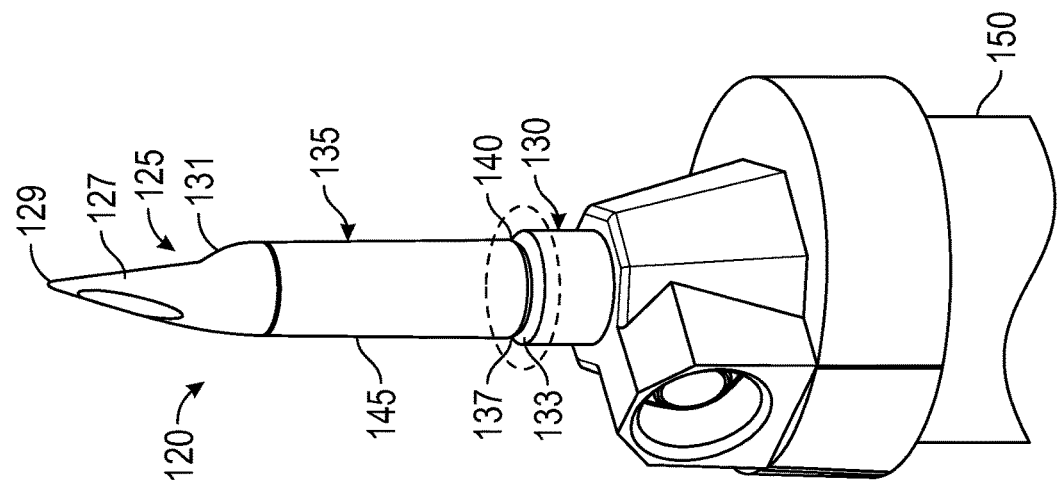
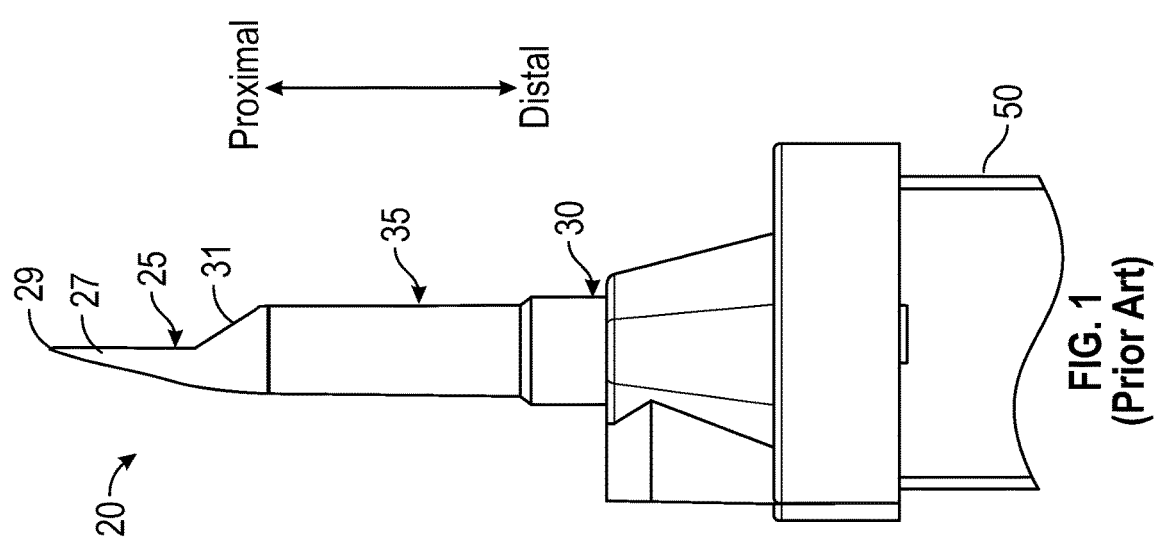
FIG. 2B
FIG. 2A
FIG. 1 (Prior Art)

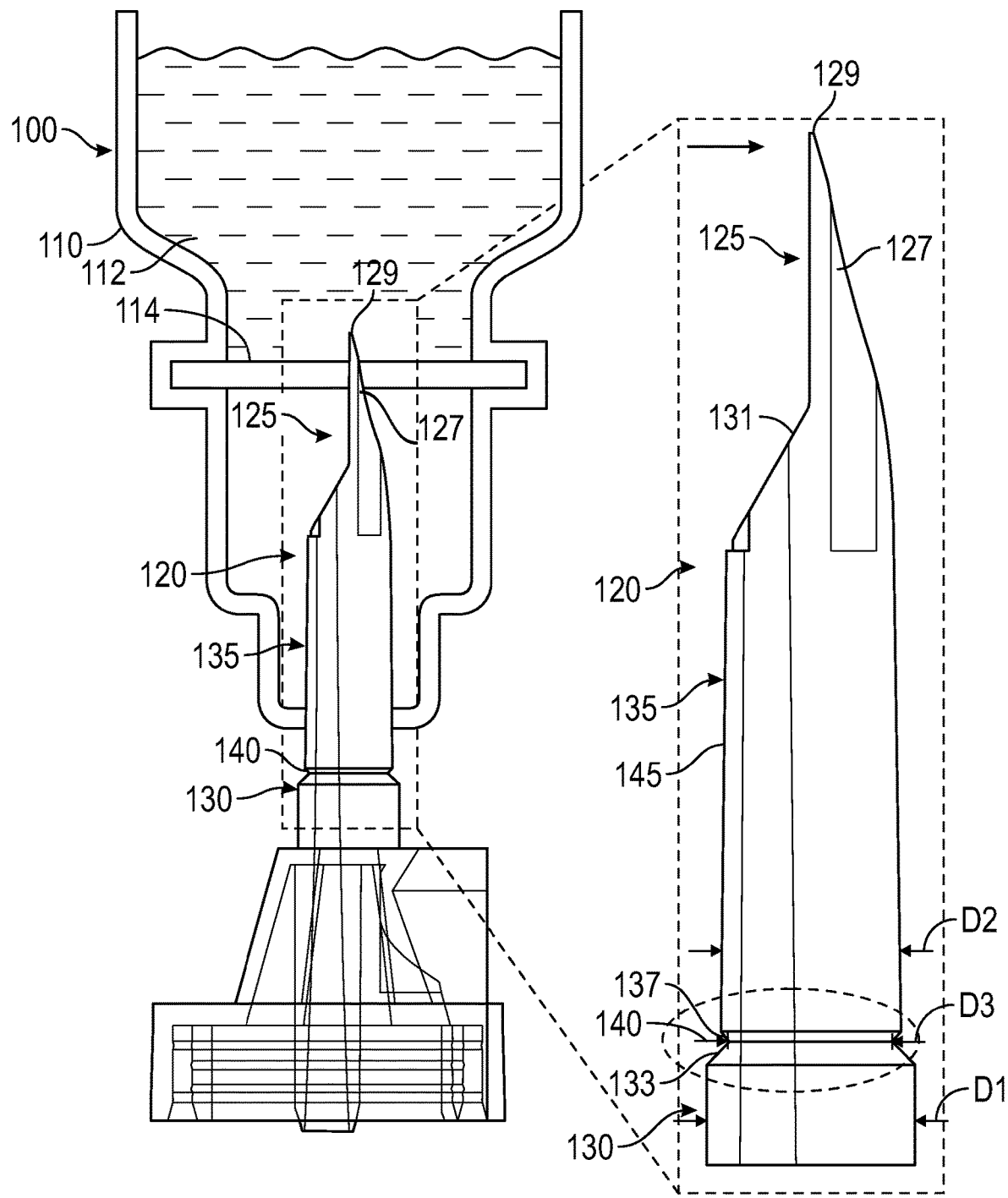
FIG. 2C  FIG. 2D

SAFETY DRIP CHAMBER SPIKE WITH BREAKABLE FEATURE

TECHNICAL FIELD

The present disclosure generally relates to IV set components, and more particularly to IV spikes having safety features for post-infusion usage disposal.

BACKGROUND

One of the most widely used methods of medical therapy is the intravenous (IV) infusion of liquid medicaments and/or nutrients into the bloodstream of a patient. A familiar apparatus that is used in many IV infusion applications is an IV container, such as an IV bag or bottle, which contains the liquid to be infused into the patient.

When the IV container is a bag or bottle, a rigid, hollow, sharpened IV spike is pushed into the bag to establish a pathway for fluid communication through which the liquid can flow out of the bag. The spike is usually inserted into the bag through a sealed membrane, commonly referred to as a port. In turn, the spike is connected to or formed integrally with an inlet port of a small, elongated, transparent hollow container familiarly referred to as a "drip chamber," with the fluid pathway of the spike in fluid communication with an interior of the drip chamber.

Improper disposal of the IV set after infusion completion in hospitals may be a potential source of infection due to the clinician or other healthcare professional being injured by the sharp tip of the IV spike.

SUMMARY

In accordance with various embodiments of the present disclosure, an intravenous (IV) spike for administering a medicinal fluid from a container may include a head portion at a proximal end thereof, a base portion at a distal end thereof, and an elongate body portion connecting the head and the base portions. The elongate body may be configured to be coupled to the container. The IV spike may further include a radial notch extending at least partially along a circumference of an outer surface of the elongate body portion. The radial notch may be recessed radially inward from the outer surface.

In accordance with various embodiments of the present disclosure, an intravenous (IV) spike assembly for administering a medicinal fluid from a container into a drip chamber while preventing spike injury may include a spike including head portion, a base portion, and an elongate body portion connecting the head and base portions, and a spike cover. The spike cover may have an elongate body for housing the spike, and a base. The base of the spike cover and the base portion of the spike may have complementary engagement features for interlocking the spike and the spike cover.

In accordance with various embodiments of the present disclosure, a method of manufacturing a spike for an intravenous (IV) drip system may include providing an elongate body with a head having a spike tip at a proximal end thereof and a base at a distal end thereof. The method may further include forming a radial notch recessed radially inward from an outer surface of the elongate body.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 1 depicts a perspective view of a conventional IV spike.

FIG. 2A depicts a perspective view of an IV spike, in accordance with some embodiments of the present disclosure.

FIG. 2B depicts a cross-sectional view of the IV spike of FIG. 2A, in accordance with some embodiments of the present disclosure.

FIG. 2C depicts an IV set that includes an IV container which is spiked by an IV spike in accordance with some embodiments of the present disclosure.

FIG. 2D is an enlarged partial perspective view of the IV spike of FIG. 2C.

DETAILED DESCRIPTION

Figure 3C:
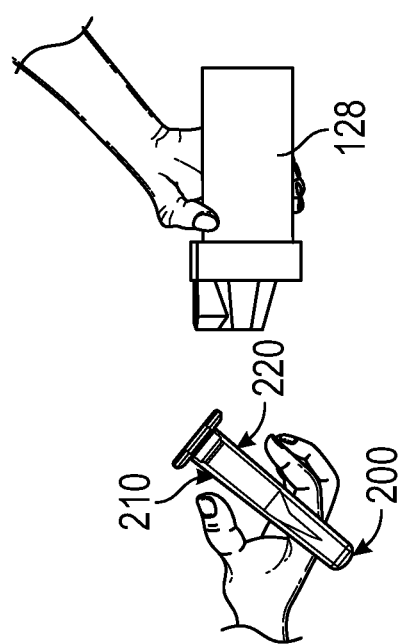
FIGS. 3B and 3C depict a method of safely disconnecting the IV spike after infusion is complete, in accordance with some embodiments of the present disclosure.

Various embodiments of the present disclosure are directed to providing IV spikes for puncturing ("spiking") membranes of IV fluid bags and bottles, where the IV spikes have improved breakable features for facilitating easier breakage of the IV spike while retaining the sharp portion of the IV spike in a container, e.g., an IV fluid bag, or spike cap.

According to various embodiments of the present disclosure, an IV spike may include a head portion with a puncture tip, a base portion, and an elongate body portion connecting the head and the base portions. The elongate body may be configured to be coupled to a container, e.g., an IV fluid bag or bottle. The IV spike may further include a radial notch extending along a circumference of an outer surface of the elongate body portion. The radial notch may be recessed radially inward from the outer surface and define a decreased or reduced cross-sectional area of the IV spike between the elongate body portion and the base portion. Due to the reduced cross-sectional area, a weak or failure point of the IV spike may be created at the location of the radial notch.

Accordingly, advantageously, when a force is applied to break the IV spike for disposal, stress concentration at the failure point allows for the IV spike to be broken using lower force than the currently existing IV spike which does not incorporate a radial notch. Further advantageously, since the IV spike of the various embodiments described herein may be mounted in the IV fluid container, once the IV spike fails and is broken at the radial notch, the elongate body portion and the head portion having the sharp puncture tip may safely remain in the IV fluid container. Accordingly, injury to the clinician or other healthcare worker as a result of being pricked or otherwise pierced by the sharp puncture tip of the IV spike may be avoided.

According to various embodiments of the present disclosure, an intravenous (IV) spike assembly for administering a medicinal fluid from a container into a drip chamber while preventing spike injury may include a spike having head portion, a base portion, and an elongate body portion connecting the head and base portions. The IV spike assembly may further include a spike cover having an elongate body for housing or otherwise covering the spike from exposure to a user, and a base. In some embodiments, the base of the spike cover and the base portion of the spike may have complementary engagement features for interlocking the spike and the spike cover. The aforementioned engagement features may be advantageous in providing a secure coupling or engagement between the IV spike and the spike cap such that the clinician or other healthcare worker may be able to disconnect or break the IV spike by exerting a breaking force or load on the spike cap versus having to apply the breaking force directly to the IV spike. Since the IV spike and the spike cap are engaged or otherwise interlocked at the bases, application of the breaking force to the spike cap would cause a corresponding breaking force to be applied to the IV spike so as to safely disconnect or remove the IV spike within the spike cap. Accordingly, injury to the clinician or other healthcare worker as a result of being pricked or otherwise pierced by the sharp puncture tip of the IV spike 220 may be avoided.

FIG. 1 depicts a perspective view of a conventional IV spike 20. The IV container 12 may be an IV fluid bag or bottle 110 (illustrated in FIG. 2C. As depicted, the conventional IV spike 20 may generally include head portion 25, a base portion 30, and an elongate body portion 35 connecting the head and base portions 25 and 30. The conventional IV spike 20 may be configured to be coupled to a drip chamber 50. A spike 27 having a puncture tip 29 and a puncture base 31 may be disposed at the head portion 25. The puncture base 31 may have a fluid inlet at an upper end thereof. As depicted, the base portion 26 may have an outer diameter greater than an outer diameter of the elongate body portion. As such, the base portion 30 may extend radially outward from the elongate body portion.

In operation, the conventional IV spike may be coupled to and pierce the IV fluid bag or container so as to fluidly connect the IV fluid container with the drip chamber 50 and allow the IV fluid to travel from the IV fluid container to be infused to a patient via the drip chamber and various other fluid lines. After infusion of the IV fluid has been completed, the IV spike may need to be discarded. Proper disposal of the IV spike after infusion is very important, as the spike 27 with the sharp puncture tip 29, if mishandled, may pierce a clinician or other medical technician and could be a potential source of infection. For example, should the spike 27 be disposed with the puncture tip 29 exposed within the IV fluid container, the tip 29 of the spike 27 could pierce through the IV fluid container and potentially injure unsuspecting healthcare workers.

Therefore, it would be advantageous to have an IV spike with a configuration that would allow for the spike to be disposed of easily and safely without potential for harming the healthcare professionals. Although current IV spikes may be formed of a material having a glass fiber reinforcement to facilitate breakage of the spike after use, current IV spike designs are not optimized for clinicians to take advantage of this useful material property easily. For example, with the current IV spikes, a greater than desirable force is required for the clinician or other healthcare professional to break the conventional IV spike 20 for disposal.

It is further advantageous to have an IV spike cap mounted over the IV spike, where spike cap and the IV spike have complementary engagement features capable of allowing the spike cap to be engaged or otherwise locked to the IV spike, thereby protecting the user from inadvertent piercing when breaking the IV spike for disposal.

The various embodiments of the present disclosure are directed to providing an IV spike having the aforementioned features that are lacking in the conventional or currently existing IV spikes.

FIG. 2A depicts a perspective view of an IV spike 120, in accordance with some embodiments of the present disclosure. FIG. 2B depicts a cross-sectional view of the IV spike 120 of FIG. 2A, in accordance with some embodiments of the present disclosure. FIG. 2C depicts an IV set 100 that includes an IV container 110 which is spiked by an IV spike 120 in accordance with some embodiments of the present disclosure.

Referring to FIGS. 2A-2C, in accordance with some embodiments, the IV spike 120 may include a head portion 125 at a proximal end thereof, a base portion 130 at a distal end thereof, and an elongate body portion 135 connecting the head and the base portions 125 and 130. As depicted in FIG. 2C, the elongate body 135 may be configured to be coupled to a container 110, e.g., an IV fluid bag or bottle. As further depicted in FIG. 2C, with further reference to FIGS. 2A and 2B, the head portion 125 may include a spike head 127 disposed at the proximal end of the IV spike 120. The spike head 127 may have a puncture tip 129 and a puncture base 131 having a fluid inlet 132 at a proximal end thereof. A fluid channel 134 may extend from the fluid inlet 132, through the elongate body portion 135, and into a drip chamber 150.

In accordance with various embodiments of the present disclosure, the IV spike 120 may further include a radial notch 140 extending along a circumference of an outer surface 145 of the elongate body portion 135. The radial notch 140 may be recessed radially inward from the outer surface 145 and define a decreased cross-section of the elongate body portion 135. In some embodiments, the radial notch 140 may be recessed in and extend along an entire circumference of the outer surface 145 of the elongate body portion 135. The various embodiments of the present disclosure however are not limited to the aforementioned configuration. In some embodiments, the radial notch 140 may extend along only a portion, or extend along laterally aligned portions of the outer surface 145 of the elongate body portion 135. For example, the radial notch 140 may be in the form of two or more smaller notches laterally spaced apart from each other about the circumference of the outer surface 145 of the elongate body portion 135. For example, in some embodiments, the radial notch 140 may comprise a series of discontinuous notches, depressions, or indentations in the outer surface 145 to weaken the material and to facilitate and enable the breaking function by a healthcare professional.

In some embodiments, the radial notch 140 may extend entirely around the outer surface 145, and in some embodiments, the radial notch 140 may extend only partway around the outer surface and still provide the breaking function. For example, in some embodiments, the radial notch 140 may extend only around about three-fourths of the outer surface

145, and in some embodiments, the radial notch 140 may extend around only about one-half, one-third, or even one-quarter of the outer surface 145. In some embodiments, the radial notch 140 can be located along an inner surface of the elongate body portion 135.

In some embodiments, the radial notch 140 may be disposed on the elongate body portion 135 at a position closer to the base portion 130 than to the head portion 125. For example, in some embodiments, the radial notch 140 may be disposed between a proximal end 133 of the base portion 130 and a distal end 137 of the elongate body portion 135.

FIG. 2D is an enlarged partial perspective view of the IV spike 120 of FIG. 2C. With reference to FIG. 2D, in some embodiments, an outer diameter D1 of the base portion 130 may be greater than an outer diameter D2 of the elongate body portion 135. As such, the radial notch 140 may be formed at a position corresponding to a decrease in cross-sectional area of the IV spike 120 associated with the transition from the elongate body portion 135 to the base portion 130. Furthermore, in some embodiments, a diameter D3 of the radial notch 140 may be less than the outer diameter D2 of the elongate body portion 135. Accordingly, the radial notch 140 provides a decreased or reduced cross-sectional thickness of the IV spike 120 between the elongate body portion 125 and the base portion 130 in comparison with a cross-sectional thickness of both the elongate body portion 125 and the base portion 130. Due to the reduced cross-sectional thickness, a weak or failure point of the IV spike 120 is created at the location of the radial notch 140. Accordingly, advantageously, when a force is applied to break the IV spike 120 for disposal, stress concentration at the failure point allows for the IV spike 120 to be broken using lower force than the currently existing IV spike 20 that does not incorporate a radial notch. Further advantageously, since the IV spike 120 may be mounted in the IV fluid container 110 illustrated in FIG. 2C, once the IV spike 120 fails and is broken at the radial notch, the elongate body portion 135 and the head portion 125 having the sharp puncture tip 129 may safely remain in the IV fluid container 110. Accordingly, injury to the clinician as a result of being pricked or otherwise pierced by the sharp puncture tip 129 of the IV spike 120 may be avoided.

In accordance with some embodiments of the present disclosure, the IV spike 120 may be formed of a thermoplastics or thermosetting plastics polymer material. For example, in some embodiments the IV spike 120 may be formed of Acrylonitrile butadiene styrene (ABS) material. The IV spike 120 may further be formed with a glass fiber reinforcement material. The glass fiber reinforcement material may cause the IV spike 120 to have a brittle structure. Accordingly, the aforementioned configuration of the IV spike 120 having the radial notch 140 is advantageous in that the brittleness of the IV spike 120 may be capitalized on in the sense that the weak point or failure point created by the radial notch may allow the IV spike 120 to break more easily when subject to breaking loads as compared to the currently existing IV spike 20. Thus, the IV spike 120 of the various embodiments described herein may fail or break at lower loads or forces, advantageously reducing the risk of injury or other ergonomic issues commonly associated with clinicians having to apply a great amount of force to break the IV spike.

According to various embodiments of the present disclosure, a method of manufacturing a spike 120 for an intravenous (IV) drip system 100 may include providing an elongate body 135 with a spike tip 129 at proximal end thereof, and a base 130 at a distal end thereof. The method may further include forming a radial notch 140 recessed radially inward from an outer surface 145 of the elongate body. In some embodiments, forming the radial notch 140 may include recessing the radial notch 140 to extend along an entire circumference of the outer surface 145. In other embodiments, forming the radial notch 140 may include recessing the radial notch to extend along a portion of the circumference of outer surface 145. For example, as described above, the radial notch 140 may extend along only a portion, or extend along laterally aligned portions of the outer surface 145 of the elongate body portion 135. In these embodiments, the radial notch 140 may be in the form of two or more smaller notches laterally spaced apart from each other about the circumference of the outer surface 145 of the elongate body portion 135

In some embodiments, a method of forming the radial notch may include changing the way in which the mold for the currently existing IV spike 20 is made. For example, the manufacturing method may include re-routing insert parting line to allow mold inserts to create the radial notch 140 without compromising the original functionality of the IV spike. In some embodiments, the IV spike 220 may include an upper spike and lower spike part ultrasonically welded or bonded via adhesives or solvents. In these embodiments, the radial notch 140 may be interposed between the upper spike and the lower spike such that the radial notch 140 may still form part of the breakable feature.

In accordance with some embodiments, forming the radial notch 140 may include positioning the radial notch 140 on the elongate body portion 135 at a position closer to the base portion 130 than to the head portion 125.

Figure 3B:
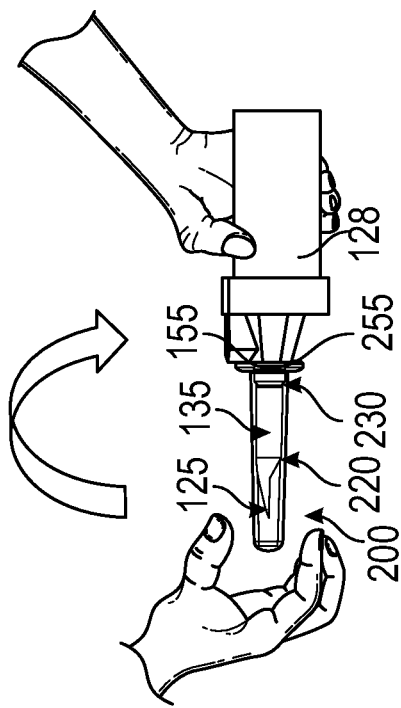
Figure 3A:
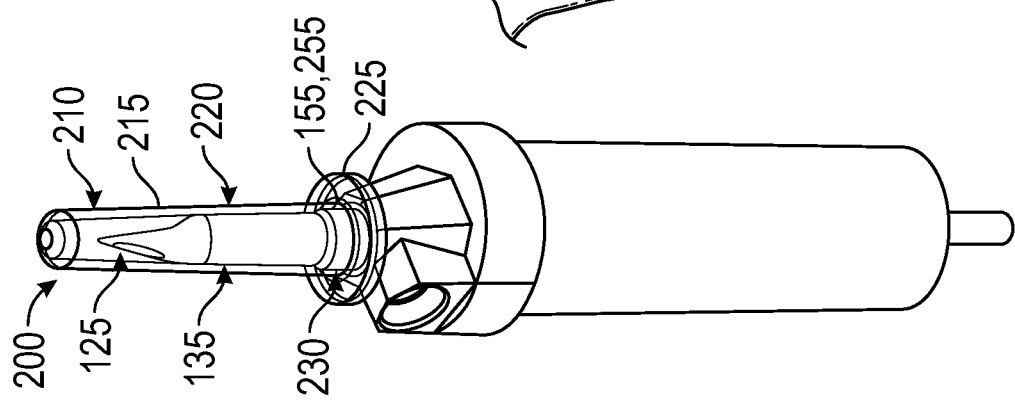
FIG. 3A depicts an IV spike assembly including an IV spike and a spike cap for protecting a user from spike injury in accordance with some embodiments of the present disclosure.

FIG. 3A depicts an IV spike assembly including an IV spike 220 and a spike cap 210 for protecting a user from spike injury in accordance with some embodiments of the present disclosure. FIGS. 3B and 3C depict a method of safely disconnecting the IV spike 220 after infusion is complete, in accordance with some embodiments of the present disclosure.

In accordance with various embodiments of the present disclosure, an intravenous (IV) spike assembly 200 for administering a medicinal fluid from a container into a drip chamber while preventing spike injury may include a spike 220 including head portion 125, a base portion 230, and an elongate body portion 135 connecting the head and base portions 125 and 130. In some embodiments, the spike 220 may have similar features to the spike 120 but with modified features as described below. In other embodiments, however, the spike 220 may have similar features to the currently existing spike 20 but with modified features as described below. As depicted in FIGS. 3A-3C, the IV spike assembly 200 may include a spike cover 210 having an elongate body 215 for housing the spike 220, and a base 225. In some embodiments, the base 225 of the spike cover 210 and the base portion 230 of the spike 220 may have complementary engagement features 155, 255 for interlocking, gripping, or otherwise holding together the spike 220 and the spike cover 210 tightly without slippage or movement. In particular, the base 225 of the spike cover 210 and the base portion 230 of the spike 220 may be designed such that the bending/breaking torque from the clinician's hands may be transmitted to the spike 220, thereby causing the spike 220 to break at the stress concentration radial notch 140.

For example, in some embodiments, the base 225 of the spike cover 210 may have a protrusion 255 and the base portion 230 of the spike 220 may have a recess 155 as the complementary engagement features. In some embodiments, the protrusion 255 of the spike cover 210 may be in the form of a sharp edge or cutter designed to be positioned around the stress concentration feature (e.g. the recess 155) such that a clinician may exert a twisting and/or bending force that will cause the spike 220 to break safely within the spike cover 210. In other embodiments, the base 225 of the spike cover 210 and the base portion 230 of the spike 220 may have complementary threads as the complementary engagement features.

The aforementioned engagement features may be advantageous in providing a secure coupling or engagement between the IV spike 220 and the spike cap 210 such that the clinician or other healthcare worker may be able to disconnect or break the IV spike 220 by exerting a breaking force or load on the spike cap 210 versus having to apply the breaking force directly to the IV spike 220. Because the IV spike 220 and the spike cap 210 are engaged or otherwise interlocked at the bases, application of the breaking force to the spike cap 210 (as illustrated in FIG. 3B) would cause a corresponding breaking force to be applied to the IV spike 220 so as to safely disconnect or remove the IV spike 220 within the spike cap 210. Accordingly, injury to the clinician or other healthcare worker as a result of being pricked or otherwise pierced by the sharp puncture tip of the IV spike 220 may be reduced or avoided.

In accordance with some embodiments, similar to the IV spike 120 described above, the IV spike 220 may be formed of a thermoplastic polymer material. For example, in some embodiments the IV spike 220 may be formed of Acrylonitrile butadiene styrene (ABS) material. The IV spike 220 may further be formed with a glass fiber reinforcement material to facilitate breakage of the spike 220 in the spike cover 210 when a force is exerted on the spike cover. As previously described, the glass fiber reinforcement material may cause the IV spike 220 to have a brittle structure. Accordingly, the aforementioned configuration of the IV spike 220 having the spike cap 210 is advantageous in that the brittleness of the IV spike 220 in combination with the engagement or locking of the base 230 of the IV spike 220 with the base 225 of the spike cap 210 allow the IV spike to break more easily and more safely when subject to breaking loads as compared to the currently existing IV spike 20 without cover engaged with the spike base.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: An intravenous (IV) spike for administering a medicinal fluid from a container, the IV spike comprising: a head portion at a proximal end thereof, a base portion at a distal end thereof, and an elongate body portion connecting the head and base portions, the elongate body portion configured to be coupled to the container; and a radial notch extending at least partially along a circumference of an outer surface of the elongate body portion, the radial notch recessed radially inward from the outer surface.

Clause 2: The IV spike of Clause 1, wherein the head portion comprises a spike head disposed at the proximal end, the spike head having a puncture tip and a puncture base having a fluid inlet at an upper end thereof, wherein a fluid channel extends from the fluid inlet, through the elongate body portion, and into a drip chamber.

Clause 3: The IV spike of Clause 1, wherein the radial notch is disposed on the elongate body portion at a position closer to the base portion than to the head portion.

Clause 4: The IV spike of Clause 3, wherein the radial notch is disposed between a proximal end of the base portion and a distal end of the elongate body portion.

Clause 5: The IV spike of Clause 4, wherein an outer diameter of the base portion is greater than an outer diameter of the elongate body portion, and the radial notch is formed at a position corresponding to a decrease in cross-sectional area associated with a transition from the base portion to the elongate body portion.

Clause 6: The IV spike of Clause 1, wherein the radial notch extends along an entire circumference of the outer surface of the elongate body portion.

Clause 7: The IV spike of Clause 1, wherein an outer diameter of the base portion is greater than an outer diameter of the elongate body portion, and a diameter of the radial notch is less than the outer diameter of the elongate body portion.

Clause 8: The IV spike of Clause 1, wherein the IV spike comprises a thermoplastic polymer material.

Clause 9: The IV spike of Clause 8, wherein the thermoplastic polymer material comprises Acrylonitrile butadiene styrene (ABS).

Clause 10: The IV spike of Clause 8, wherein the IV spike further comprises a glass fiber reinforcement material to facilitate breakage of the elongate body portion in the container as the radial notch creates a stress concentration point when a force is exerted on the spike.

Clause 11: An intravenous (IV) spike assembly for administering a medicinal fluid from a container into a drip chamber while preventing spike injury, the IV spike assembly comprising: a spike including head portion, a base portion, and an elongate body portion connecting the head and base portions; and a spike cover comprising an elongate body for housing the spike, and a base, wherein the base of the spike cover and the base portion of the spike comprise complementary engagement features for interlocking the spike and the spike cover.

Clause 12: The IV spike assembly of Clause 11, wherein the base of the spike cover comprises a protrusion and the base portion of the spike comprises a recess as the complementary engagement features.

Clause 13: The IV spike assembly of Clause 11, wherein the base of the spike cover and the base portion of the spike comprise complementary threads as the complementary engagement features.

Clause 14: The IV spike assembly of Clause 11, wherein the spike further includes: a puncture tip and a puncture base having a fluid inlet at the head portion of the elongate body portion; and a fluid channel extending from the puncture base, through the elongate body portion, and into the drip chamber.

Clause 15: The IV spike assembly of Clause 11, wherein the spike comprises a thermoplastic polymer material.

Clause 16: The IV spike assembly of Clause 15, wherein the spike further comprises a glass fiber reinforcement material to facilitate breakage of the spike in the spike cover.

Clause 17: A method of manufacturing a spike for an intravenous (IV) drip system, the method comprising: providing an elongate body with a head having a spike tip at a proximal end thereof and a base at a distal end thereof; and forming a radial notch recessed radially inward from an outer surface of the of the elongate body.

Clause 18: The method of Clause 17, wherein forming the radial notch comprises recessing the radial notch along a portion of a circumference of the outer surface.

Clause 19: The method of Clause 17, wherein forming the radial notch comprises recessing the radial notch along an entire circumference of the outer surface.

Clause 20: The method of Clause 17, wherein forming the radial notch comprises positioning the radial notch on the elongate body at a position closer to the base than to the head.

As used herein, the terms "tubing," "fluid line," and any variation thereof refers to medical lines or tubes used to deliver liquids, solvents, or fluids (including gas) to or from a patient under medical care. For example, fluid lines (tubing) may be used for intravenous (IV) delivery of fluids, fluid drainage, oxygen delivery, a combination thereof, and the like.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An intravenous (IV) spike for administering a medicinal fluid from a container, the IV spike comprising:
   a head portion at a proximal end thereof, a base portion at a distal end thereof, and an elongate body portion connecting the head and base portions, the base portion having an outer diameter that is greater than an outer diameter of the elongate body portion, wherein the elongate body portion is configured to be coupled to the container; and
   a radial notch extending at least partially along a circumference of an outer surface of the IV spike, and from a proximal end of the base portion and a distal end of the elongate body portion such that the radial notch is positioned at a decrease in cross-sectional area at the transition from the base portion to the elongate body portions, the radial notch recessed radially inward from the outer surface.

2. The IV spike of claim 1, wherein the head portion comprises a spike head disposed at the proximal end, the spike head having a puncture tip and a puncture base having a fluid inlet at an upper end thereof, wherein a fluid channel extends from the fluid inlet, through the elongate body portion, and into a drip chamber.

3. The IV spike of claim 1, wherein the radial notch is disposed on the elongate body portion at a position closer to the base portion than to the head portion.

4. The IV spike of claim 1, wherein the radial notch extends along an entire circumference of the outer surface of the elongate body portion.

5. The IV spike of claim 1, wherein a diameter of the radial notch is less than the outer diameter of the elongate body portion.

6. The IV spike of claim 1, wherein the IV spike comprises a thermoplastic polymer material.

7. The IV spike of claim 6, wherein the thermoplastic polymer material comprises Acrylonitrile butadiene styrene (ABS).

8. The IV spike of claim 6, wherein the IV spike further comprises a glass fiber reinforcement material to facilitate breakage of the elongate body portion in the container as the radial notch creates a stress concentration point when a force is exerted on the spike.

* * * * *